US008968728B2

(12) United States Patent
Ella et al.

(10) Patent No.: US 8,968,728 B2
(45) Date of Patent: Mar. 3, 2015

(54) CHIMERIC FUSION PROTEINS

(75) Inventors: Krishna Murthy Ella, Hyderabad (IN); Kandaswamy Sumathy, Hyderabad (IN)

(73) Assignee: Bharat Biotech International Limited (IN)

( * ) Notice: Subject to any disclaimer, the term of this patent is extended or adjusted under 35 U.S.C. 154(b) by 1092 days.

(21) Appl. No.: 12/300,150

(22) PCT Filed: May 11, 2007

(86) PCT No.: PCT/IN2007/000191
§ 371 (c)(1),
(2), (4) Date: Mar. 24, 2009

(87) PCT Pub. No.: WO2007/132481
PCT Pub. Date: Nov. 22, 2007

(65) Prior Publication Data
US 2010/0015123 A1     Jan. 21, 2010

(30) Foreign Application Priority Data

May 12, 2006   (IN) .............................. 843/CHE/2006

(51) Int. Cl.
*A61K 38/48*   (2006.01)
*C12N 9/72*    (2006.01)
*C12N 9/70*    (2006.01)
*C12P 21/04*   (2006.01)
*C07H 21/04*   (2006.01)
*C07K 1/00*    (2006.01)
*C07K 14/31*   (2006.01)

(52) U.S. Cl.
CPC ........... *C07K 14/31* (2013.01); *C07K 2319/035* (2013.01)
USPC ....... 424/94.64; 435/215; 435/216; 435/69.7; 536/23.2; 536/23.4; 530/350

(58) Field of Classification Search
USPC ...................... 424/94.64; 435/215, 216, 69.7; 536/23.2, 23.4; 530/350
See application file for complete search history.

(56) References Cited

U.S. PATENT DOCUMENTS

| | | | | |
|---|---|---|---|---|
| 6,423,512 | B1 * | 7/2002 | Digan et al. ................. | 435/69.7 |
| 6,821,948 | B1 * | 11/2004 | Braun et al. .................... | 514/1.2 |
| 7,332,159 | B2 * | 2/2008 | Labhasetwar et al. ........ | 424/94.4 |
| 2006/0127389 | A1 * | 6/2006 | Shi et al. ..................... | 424/94.64 |

OTHER PUBLICATIONS

Wells, (Biochemistry, vol. 29, pp. 8509-8517, 1990.*
Jin et al. (J. of Immunol. vol. 172, 1169-1179, 2004).*
Xia et al (Nature Biotech., vol. 19, Jul. 2001, pp. 640-644).*
Wiktorek-Smagur, (World J. Microbiol Biotechnol., 2011, vol. 27, pp. 1341-1347).*
Asoh, S. et al. (2002) "Protein Against Ischemic Brain injury by Protein Therapeutics" *Proc. Natl Acad. Sci USA* 99(26):17107-17112.
Badimon L. and Badimon JJ. (1989) "Mechanisms of Arterial Thrombosis in Nonparaellel Streamlines: Platelet thrombi Grow on the Apex of Stenotic Severely Injured Vessel Wall" *J. Clin. Invest.* 84:1134-1144.
Cao, G. et al. (2002) "In vivo Delivery of a Bcl-xL Fusion Protein Containing the TAT Protein Transduction Domain Protects Against Ischemic Brain Injury and Neuronal Apoptosis" *J. Neurosci.* 22(13):5423-5431.
Herbert, T.P., Fahraeus, R., Prescott, A., Lane, D.P. & Proud, C.G. (2000) "Rapid Induction of Apoptosis Mediated by Peptides that Bind Initiation Factor eIF4E." *Curr Biol.* 10:793-796.
Ho A., Schwarze S.R., Mermelstein S.UJ., Waksman G., Dowdy S.F. (2001) "Synthetic Protein Transduction Domains: Enhanced Transduction Potential in Vitro and in Vivo" *Cancer Research* 61:474-477.
Mainguy, G. et al. (2000) "An Induction Gene Trap for Identifying a Homeoprotein-regulated Locus" *Nature Biotechnol.* 18:746-749.
Mazel, M. et al. (2001) "Doxorubicin-Peptide Conjugates Overcome Multidrug Resistance" *Anticancer Drugs* 12:107-116.
Rousselle, C. et al. (2001) "Enhanced Delivery of Doxorubicin into the Brain via a Peptide-vector-mediated Strategy: Saturation Kinetics and Specificity" *J. Pharmacol. Exp. Ther.* 296(1):124-131.
Rousselle, C. et al. (2000) "New Advances in the Transport of Doxorubicin Through the Blood-brain Barrier by a Peptide Vector-Mediated Strategy" *Mol. Pharmacol* 57:679-686.
Schwarze, S.R., Ho, A., Vocero-Akbani, A & Dowdy, S.F. (1999) "In Vivo Protein Transduction: Delivery of a Biologically Active Protein into the Mouse" *Science* 285:1569-1572.

* cited by examiner

*Primary Examiner* — Ganapathirama Raghu
(74) *Attorney, Agent, or Firm* — Roger Emerson; Emerson Thomson Bennett, LLC

(57) ABSTRACT

New thrombolytic protein molecules such as recombinant staphylokinase or streptokinase, urokinase, tissue plasminogen activator and the like, and suitable variants thereof, for targeting to brain tissue or any other tissue by either fusing to, or by synthesizing the candidate thrombolytic molecule(s) with a protein sequence comprising a strong amphipathic alpha helix containing protein transduction domain. Thrombolytic protein molecule(s) so engineered with the protein transduction domain is useful for enhanced uptake of such protein thrombolytic molecule(s) across the cell membranes and tissues including the blood brain barrier and find their use in the treatment of vascular thrombosis including cerebrovascular disorders caused by cerebral thrombosis or cerebral haemorrhage when used a as a therapeutic. The design and processes for cloning, expression, purification and protein transduction of such proteins across cell membranes.

21 Claims, 6 Drawing Sheets a) eGFP-PTD b) Control GFP c) SAK-PTD

2A. PTD-SAK d) Control SAK

Fig. 2: A- 100 bp ladder; B- Final PCR amplified product of SAK-PTD ~ 429 bp

Fig 3. A- 100 bp ladder; B – Final PCR amplified product of eGFP-PTD ial filing date of May 11, 2007, which is based on Indian Patent

SEQUENCE LISTING

```
<160> NUMBER OF SEQ ID NOS: 15

<210> SEQ ID NO 1
<211> LENGTH: 127
<212> TYPE: PRT
<213> ORGANISM: Staphylococcus aureus

<400> SEQUENCE: 1

Met Lys Gly Asp Asp Ala Ser Tyr Phe Glu Pro Thr Gly Pro Tyr Leu
1               5                   10                  15

Met Val Asn Val Thr Gly Val Asp Gly Lys Gly Asn Glu Ile Leu Ser
            20                  25                  30

Pro His Tyr Val Glu Phe Pro Ile Lys Pro Gly Thr Thr Leu Thr Lys
        35                  40                  45

Glu Lys Ile Glu Tyr Tyr Val Glu Trp Ala Leu Asp Ala Thr Ala Tyr
    50                  55                  60

Lys Glu Phe Arg Val Val Glu Leu Asp Pro Ser Ala Lys Ile Glu Val
65                  70                  75                  80

Thr Tyr Tyr Asp Lys Asn Lys Lys Glu Glu Thr Lys Ser Phe Pro
                85                  90                  95

Ile Thr Glu Lys Gly Phe Val Val Pro Asp Leu Ser Glu His Ile Lys
            100                 105                 110
```

Asn Pro Gly Phe Asn Leu Ile Thr Lys Val Val Ile Glu Lys Lys
        115                 120                 125

<210> SEQ ID NO 2
<211> LENGTH: 143
<212> TYPE: PRT
<213> ORGANISM: Artificial Sequence
<220> FEATURE:
<223> OTHER INFORMATION: SAK-PTD fusion protein from artificial and
      natural structural modules: residues 1-17 are completely
      synthesized, residues 17-143 are from Staphylococcus aureus

<400> SEQUENCE: 2

Met Gly Tyr Ala Arg Ala Ala Ala Arg Gln Ala Arg Ala Gly Gly Gly
1               5                   10                  15

Ser Lys Gly Asp Asp Ala Ser Tyr Phe Glu Pro Thr Gly Pro Tyr Leu
            20                  25                  30

Met Val Asn Val Thr Gly Val Asp Gly Lys Gly Asn Glu Ile Leu Ser
            35                  40                  45

Pro His Tyr Val Glu Phe Pro Ile Lys Pro Gly Thr Thr Leu Thr Lys
        50                  55                  60

Glu Lys Ile Glu Tyr Tyr Val Glu Trp Ala Leu Asp Ala Thr Ala Tyr
65                  70                  75                  80

Lys Glu Phe Arg Val Val Glu Leu Asp Pro Ser Ala Lys Ile Glu Val
                85                  90                  95

Thr Tyr Tyr Asp Lys Asn Lys Lys Glu Glu Thr Lys Ser Phe Pro
            100                 105                 110

Ile Thr Glu Lys Gly Phe Val Val Pro Asp Leu Ser Glu His Ile Lys
            115                 120                 125

Asn Pro Gly Phe Asn Leu Ile Thr Lys Val Val Ile Glu Lys Lys
            130                 135                 140

<210> SEQ ID NO 3
<211> LENGTH: 143
<212> TYPE: PRT
<213> ORGANISM: Artificial Sequence
<220> FEATURE:
<223> OTHER INFORMATION: SAK-PTD fusion protein from artificial and
      natural structural modules: residues 1-17 are completely
      synthesized, residues 17-143 are from Staphylococcus aureus

<400> SEQUENCE: 3

Met Gly Tyr Gly Arg Lys Lys Arg Gln Arg Arg Arg Gly Gly Gly
1               5                   10                  15

Ser Lys Gly Asp Asp Ala Ser Tyr Phe Glu Pro Thr Gly Pro Tyr Leu
            20                  25                  30

Met Val Asn Val Thr Gly Val Asp Gly Lys Gly Asn Glu Ile Leu Ser
            35                  40                  45

Pro His Tyr Val Glu Phe Pro Ile Lys Pro Gly Thr Thr Leu Thr Lys
        50                  55                  60

Glu Lys Ile Glu Tyr Tyr Val Glu Trp Ala Leu Asp Ala Thr Ala Tyr
65                  70                  75                  80

Lys Glu Phe Arg Val Val Glu Leu Asp Pro Ser Ala Lys Ile Glu Val
                85                  90                  95

Thr Tyr Tyr Asp Lys Asn Lys Lys Glu Glu Thr Lys Ser Phe Pro
            100                 105                 110

Ile Thr Glu Lys Gly Phe Val Val Pro Asp Leu Ser Glu His Ile Lys
            115                 120                 125

```
Asn Pro Gly Phe Asn Leu Ile Thr Lys Val Val Ile Glu Lys Lys
    130                 135                 140

<210> SEQ ID NO 4
<211> LENGTH: 11
<212> TYPE: PRT
<213> ORGANISM: Artificial Sequence
<220> FEATURE:
<223> OTHER INFORMATION: Protein Transduction Doman polypeptide

<400> SEQUENCE: 4

Tyr Ala Arg Ala Ala Ala Arg Gln Ala Arg Ala
1               5                   10

<210> SEQ ID NO 5
<211> LENGTH: 11
<212> TYPE: PRT
<213> ORGANISM: Artificial Sequence
<220> FEATURE:
<223> OTHER INFORMATION: aminio acids 47 to 57 of the HIV TAT protein

<400> SEQUENCE: 5

Tyr Gly Arg Lys Lys Arg Arg Gln Arg Arg Arg
1               5                   10

<210> SEQ ID NO 6
<211> LENGTH: 4
<212> TYPE: PRT
<213> ORGANISM: Artificial Sequence
<220> FEATURE:
<223> OTHER INFORMATION: Linker polypeptide

<400> SEQUENCE: 6

Gly Gly Gly Ser
1

<210> SEQ ID NO 7
<211> LENGTH: 37
<212> TYPE: DNA
<213> ORGANISM: Artificial Sequence
<220> FEATURE:
<223> OTHER INFORMATION: Primer

<400> SEQUENCE: 7
ggtggtggtt cgaaaggcga tgacgcgagt tattttg                     37

<210> SEQ ID NO 8
<211> LENGTH: 31
<212> TYPE: DNA
<213> ORGANISM: Artificial Sequence
<220> FEATURE:
<223> OTHER INFORMATION: Primer

<400> SEQUENCE: 8
cgtcaggcgc gtgcgggtgg tggttcgaaa g                           31

<210> SEQ ID NO 9
<211> LENGTH: 28
<212> TYPE: DNA
<213> ORGANISM: Artificial Sequence
<220> FEATURE:
<223> OTHER INFORMATION: Primer

<400> SEQUENCE: 9
gcacgtgcag cagcacgtca ggcgcgtg                               28
```

```
<210> SEQ ID NO 10
<211> LENGTH: 36
<212> TYPE: DNA
<213> ORGANISM: Artificial Sequence
<220> FEATURE:
<223> OTHER INFORMATION: Primer

<400> SEQUENCE: 10
caatgaattc atatgggtta tgcacgtgca gcagca                              36

<210> SEQ ID NO 11
<211> LENGTH: 30
<212> TYPE: DNA
<213> ORGANISM: Artificial Sequence
<220> FEATURE:
<223> OTHER INFORMATION: Primer

<400> SEQUENCE: 11
cacggatcct tatttctttt ctataacaac                                     30

<210> SEQ ID NO 12
<211> LENGTH: 34
<212> TYPE: DNA
<213> ORGANISM: Artificial Sequence
<220> FEATURE:
<223> OTHER INFORMATION: Primer

<400> SEQUENCE: 12
gtacggatcc ttatctagat ccggtggatc ccgg                                34

<210> SEQ ID NO 13
<211> LENGTH: 33
<212> TYPE: DNA
<213> ORGANISM: Artificial Sequence
<220> FEATURE:
<223> OTHER INFORMATION: Primer

<400> SEQUENCE: 13
gtacgaattc atatggtgag caagggcgag gag                                 33

<210> SEQ ID NO 14
<211> LENGTH: 27
<212> TYPE: DNA
<213> ORGANISM: Artificial Sequence
<220> FEATURE:
<223> OTHER INFORMATION: Primer

<400> SEQUENCE: 14
ggtggtggtt cggtgagcaa gggcgag                                        27

<210> SEQ ID NO 15
<211> LENGTH: 30
<212> TYPE: DNA
<213> ORGANISM: Artificial Sequence
<220> FEATURE:
<223> OTHER INFORMATION: Primer

<400> SEQUENCE: 15
cgtcaggcgc gtgcgggtgg tggttcggtg                                     30
```

CHIMERIC FUSION PROTEINS

CROSS-REFERENCE TO RELATED APPLICATIONS

This is a National Stage Application of International Patent Application No. PCT/IN2007/000191, with an internationfiling date of May 11, 2007, which is based on Indian Patent Application No. 843/CHE/2006, filed May 12, 2006. The contents of these specifications are incorporated herein by reference.

BACKGROUND OF THE INVENTION

1. Field of the Invention

The present invention relates to generation of novel thrombolytic molecules with enhanced protein transduction efficiency and processes therefor.

2. Description of the Related Art

Occlusion of blood vessels occurs due to the presence of blood clots (thrombi). Thrombin that is composed of fibrin and blood cells, may form in any part of the cardiovascular system including the veins, arteries, heart and microcirculation (Badimon at al., J. Clin. Invest. 1989, 84, 1134-1144). Thrombi progressively undergo structural changes; leucocytes that are attracted by chemotactic factors released from the aggregated platelets or proteolytic fragments of plasma proteins become incorporated into the thrombi. These aggregated platelets swell and disintegrate and are gradually replaced by fibrin. These clots often affect heart and lungs and may loosen and block smaller blood vessels.

Normal and timely blood flow through the damaged blood vessels requires the use of fibrinolytic agents. See, e.g., Chesbro et al., Circulation, 1987, 76, 142-154.

Streptokinase, staphylokinase, and other thrombolytic agents such as urokinase and tissue plasminogen activators are commonly used in the treatment of myocardial infarction, pulmonary, arterial or venous thromboembolism, surgical adhesions and other such instances when thrombi are formed. Thrombolytic agents act by converting endogenous plasminogen (a proenzyme) to plasmin (an active enzyme), which lyses the clot and could be used as thrombolytic agent in vivo. Plasminogen is a single chain glycoprotein, which in its native form has an amino terminal glutamic acid. It is converted into plasmin by the cleavage of Arg-Val (560-561) peptide bond. Robbins et al., Methods in Enzymology, 1976, 45, 257-273.

In the case of cerebral hemorrhage, smaller diseased arteries may rupture and bleed into the brain. Both of these events damage the brain and are collectively referred to as strokes (cerebrovascular accidents or CVAs). A cerebral stroke normally produces a sudden onset of symptoms. Depending on the artery affected, symptoms can include paralysis, speech difficulties, and difficulty in swallowing, visual and sensory disturbances.

Cerebral thrombosis can be treated by invasive procedures that can be highly traumatic and often have low therapeutic efficiency with substantial side effects. One of the alternative methods of treating stroke could involve employing one or more fibrinolytic agents such as streptokinase, acylated plasminogen-streptokinase complex, staphylokinase, urokinase, tissue plasminogen activator, and the like in cerebral tissue.

However there is a limitation in the uptake of such protein molecules into brain because of the blood-brain barrier that is impervious to most if not of all the proteins.

Blood brain barrier is the limiting factor in virtually all brain drug development programs since >98% of all small molecules and 100% of the large protein molecules do not cross the blood brain barrier. At the molecular level, the blood brain barrier consists of microvascular endothelial cells lining the brain microvessels together with closely associated astrocytic end feet processes. The microcapillary endothelium is characterized by the presence of tight junctions between the cerebral endothelial cells that form a diffusion barrier, which selectively excludes most blood-borne substances from the brain tissue.

The distribution of drug in brain requires a transvascular route and this approach requires the ability to undergo transport across the blood brain barrier. There has been success in transduction of protein molecules across the blood brain barrier by fusing or synthesizing proteins with protein transduction domain (PTD) to transport hydrophilic cargoes. Transduction peptides, in particular SynB (Rousselle et al., J. Pharmacol. Exp. Ther., 2001, 296, 124-131), Penetratin (Mazel et al., Anticancer Drugs, 2001, 12, 107-116; Rousselle et al., Mol. Pharmacol., 2000, 57, 679-686), and TAT peptides (Schwarze et al., Science, 1999, 285, 1569-1572; Cao et al., J. Neurosci. 2002, 22, 5423-5431; and Asoh et al., Proc. Natl Acad. Sci USA, 2002, 99, 17107-17112) markedly increase access to the brain. For example, targeting anti-apoptotic peptides (Cao et al., 2002; Asoh et al. 2002) into the brain has been used to provide protection against ischemic injury. A homeodomain-derived peptide to internalize C3-transferase (the small GTP-binding protein that antagonizes Rho) and reversed neuronal death in the spinal cord by 50% after injury (Mainguy et al., Nature Biotechnol., 2000, 18, 746-749). A cell penetrating peptide targeting eukaryotic initiation factor has been used to induce apoptosis in cancer cells (Herbert et al., Curr. Biol., 2000, 10, 793-796).

The use of cell penetrating peptides in the target molecules offers an unlimited scope for protein therapeutics. This invention is one such example of using this technique for designing novel thrombolytic molecules for dissolving thrombi in vasculature and in tissues including the cerebral tissues for indications of cerebral thrombosis.

BRIEF SUMMARY OF THE INVENTION

The main object of the present invention is to provide novel thrombolytic agents engineered with protein transduction domain for enhanced uptake of such proteins into tissues including the blood brain barrier for treatment of thrombosis in vasculature and tissues including cerebral tissues. The suitable thrombolytic molecules include streptokinase, urokinase, staphylokinase, tissue plasminogen activator and the like and are suitable to their variants thereof, with demonstrated potential to dissolve the thrombi.

Another object is to provide a new recombinant protein by either fusing to, or by synthesizing the candidate thrombolytic molecule(s) with a protein sequence comprising a strong amphipathic alpha helix containing protein transduction domain. Further, the protein transduction domain (PTD) fused either at the N or C terminus of the protein thrombolytic molecule with or without intervening linker sequence could include either of the following sequences: SEQ ID NO. 5, YGRKKRRQRRR, corresponding to that of amino acids 47 to 57 of the HIV TAT protein or a protein sequence synthetically optimized to include a strong amphipathic helix for enhancing transduction into cells and tissues, and potentially across the blood brain barrier into cerebral tissues.

The recombinant thrombolytic protein molecule used for incorporating a protein transduction domain is mature staphylokinase. In accordance with the processes described, the protein is cloned and expressed as a recombinant protein in E.

*coli* as an intracellular protein and can be expressed in eukaryotic expression systems as well. The expressed protein is further isolated and purified for use in pharmaceutical formulations.

The invention provides a process of designing, cloning, recombinant expression and purification of such thrombolytic molecules. Yet other object of the invention is to provide thrombolytic protein molecule(s) so engineered with the protein transduction domain have their use in the treatment of thrombosis in vasculature including the blood vessels lining the brain tissue such as in cerebrovascular accidents caused by cerebral thrombosis or cerebral hemorrhage or cerebral stroke or any condition that requires dissolving the thrombi formed by seepage of blood into tissues including cerebral tissues.

DETAILED DESCRIPTION OF THE INVENTION

Figure 1:
FIG. 1 is a graphical depiction of the design of the eGFP-PTD and SAK-PTD proteins, wherein eGFP refers to Green Fluorescent Protein; PTD refers to Protein Transduction Domain of the amino acid sequence of SEQ ID NO. 4, YARAAARQARA or SEQ ID NO. 5, YGRKKRRQRRR; SAK refers to the region encoding the 127 amino acid residue of staphylokinase beginning with N-terminal sequence KGDDA of SEQ ID NO. 1; L refers to Linker region of SEQ ID NO. 6, Gly-Gly-Gly-Ser (GGGS); eGFP-PTD refers to the protein with added PTD domain at the 5' end of eGFP, and SAK-PTD refers to the protein with the added PTD domain at the 5' end of SAK.
Figure 1:
Figure 1:
Figure 1:
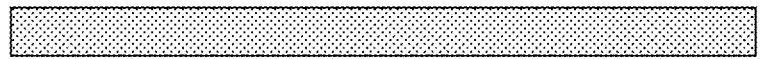

The invention discloses a process by which any protein thrombolytic agent like streptokinase, staphylokinase, tissue plasminogen activator, urokinase, and any variants and derivatives thereof, are suitable to be fused to, or synthesized with a protein transduction domain either at the N-terminus or C-terminus, either with or without a linker sequence separating the therapeutic protein from the protein transduction domain.

The addition of the linker sequences between two functional domains of a protein aids proper folding of the domains thereby helps in retaining functional activity. The protein transduction domain can be introduced at any region of the protein other than the N- or C-terminus without loss of functional activity.

The therapeutic molecule of the present invention for tissue targeting is derived from mature staphylokinase that carries a deletion of first ten amino acids at the N-terminal end (DELTA 10 SAK), and beginning with the sequence NH2-terminal Lys-Gly-Asp and whose fibrinolytic activity is same as that of the mature staphylokinase (mSAK).

Staphylokinase protein modified to include a Protein Transduction Domain is synthesized by polymerase chain reaction (PCR) with either of the sequence comprising the amino acids 47-57 of the HIV TAT protein of the sequence YGRKKRRQRRR (SEQ ID NO: 5), or a sequence synthetically optimized to include a strong amphipathic helix with protein transduction characteristics. One such sequence mentioned in the embodiment of the invention is the amino acid sequence YARAAARQARA (SEQ ID NO: 4). The protein transduction domain could be anywhere between 5 to 25 amino acids in length. Those skilled in the art also know that any amino acid sequence with cell penetrating property could be used to fuse to the protein to enhance transduction potential across cell membrane and into tissues including cerebral tissues by crossing the blood brain barrier.

The design further includes a linker sequence of amino acids separating the protein transduction domain from the therapeutic protein. The protein transduction domain and the linker sequences are added by PCR and the final PCR product is cloned into an expression vector such as pET11B for expression in *E. coli* host as an intracellular protein. Those skilled in the art would know that protein could also be expressed as a secretary protein in *E. coli* or in a eukaryotic expression system such as yeast, insect or mammalian cells either as a secretary protein or as an intracellular protein.

The thrombolytic protein molecule so engineered with protein transduction domain either at the N-terminus at the C-terminus could also include the mature proteins of streptokinase or recombinant tissue plasminogen activator or urokinase or anisoylated plasminogen streptokinase and the like, that have thrombolytic activity and derivatives or variants of the above including that of staphylokinase whose sequences have been modified to reduce the immunogenicity and/or enhance the fibrinolytic activity of the proteins.

The expressed recombinant protein is purified either from the soluble fraction of the *E. coli* cells transformed with the plasmid encoding staphylokinase with protein transduction domain or from inclusion bodies after denaturing with urea, guanidine hydrochloride, or any other suitable denaturing agent.

The soluble or solubilized protein is purified by column chromatography and the purified protein is formulated in a suitable buffer for systemic injection. The purified recombinant protein is characterized by bioassay, and analytical techniques that includes among other techniques, HPLC and SDS-PAGE. This method is also applicable to any other thrombolytic protein molecule or their derivatives and variants thereof, such as recombinant mature streptokinase, urokinase, tissue plasminogen activator and the like, and all the variants and derivatives of staphylokinase that is engineered for reduced immunogenicity and/or enhanced fibrinolytic activity.

The protein transduction domain is useful for enhanced uptake of such protein thrombolytic molecule(s) across all tissues including the blood brain barrier and find their application for therapeutic treatment of the cerebrovascular disorders such as cerebral hemorrhage, cerebral thrombosis and cerebral stroke or any condition that requires dissolving the thrombi formed in blood vessels lining the brain tissue.

SEQ ID NO: 1
MKGDDASYFEPTGPYLMVNVTGVDGKGNEILSPHYVEFPIKPGTTLTKEK

IEYYVEWALDATAYKEFRVVELDPSAKIEVTYYDKNKKKEETKSFPITEK

GFVVPDLSEHIKNPGFNLITKVVIEKK

-continued

SEQ ID NO: 2
MGYARAAARQARAGGGSKGDDASYFEPTGPYLMVNVTGVDGKGNEILS

PHYVEFPIKPGTTLTKEKIEYYVEWALDATAYKEFRVVELDPSAKIEVTY

YDKNKKKEETKSFPITEKGFVVPDLSEHIKNPGFNLITKVVIEKK

SEQ ID NO: 3
MGYGRKKRRQRRRGGGSKGDDASYFEPTGPYLMVNVTGVDGKGNEILS

PHYVEFPIKPGTTLTKEKIEYYVEWALDATAYKEFRVVELDPSAKIEVTY

YDKNKKKEETKSFPITEKGFVVPDLSEHIKNPGFNLITKVVIEKK

EXAMPLES

Example 1

Design of the Novel Staphylokinase by Addition of a Protein Transduction Domain

The design includes adding a protein transduction domain (PTD) of 11 amino acid residues to the N-terminus of staphylokinase (SEQ ID NO: 1). The PTD domain and staphylokinase are separated by an amino acid linker of the sequence Gly-Gly-Gly-Ser (SEQ ID NO: 6).

Native staphylokinase molecule without PTD domain was used as a control. eGFP (Green Fluorescent Protein) consisting of PTD domain of similar sequence was used as a positive control in the experiments. The cloning strategy for both the SAK-PTD and eGFP-PTD were similar. The design of SAK-PTD and eGFP-PTD are depicted in FIG. 1.

The region encoding the 127 amino acid residue of staphylokinase beginning with N-terminal sequence KGDDA is referred to in this invention as staphylokinase or SAK.

The protein with the added PTD domain at the 5' end is referred to as SAK-PTD. The protein with added PTD domain at the 5' end of eGFP is referred to as eGFP-PTD.

Example 2

Cloning and Recombinant Expression of SAK-PTD and eGFP-PTD

Staphylokinase gene of SEQ ID NO. 1 cloned in plasmid pET23a was used as a template for the synthesis of SAK-PTD by Polymerase Chain Reaction (PCR). PCR amplification was carried out serially to add 4 amino acid residues of the linker sequence of SEQ ID NO. 6, Gly-Gly-Gly-Ser, and 11 amino acid residues of SEQ ID NO. 5, Tyr-Gly-Arg-Lys-Lys-ArgArg-Gln-Arg-Arg-Arg (YGRKKRRQRRR), or of SEQ ID NO. 4, Tyr-Ala-Arg-Ala-AlaAla-Arg-Gln-Ala-Arg-Ala (YARAAARQARA) at the 5' end of the staphylokinase gene to generate SAK-PTD. The PCR amplification was carried out in four steps serially with overlapping primer sets to add a total of 16 amino acid residues including the initiator Met at the 5' end. An example of the primer sets used for the generation of the final SAK-PTD fragment are:

BTNTFPISAK (SEQ ID NO. 7)-
5' GGTGGTGGTTCGAAAGGCGATGACGCGAGTTATTTTG 3';

BTNTFP2SAK (SEQ ID NO. 8)-
5' CGTCAGGCGCGTGCGGGTGGTGGTTCGAAAG 3';

BTNTFP3 (SEQ ID NO. 9)-
5' GCACGTGCAGCAGCACGTCAGGCGCGTG 3';

BTNTFP4 (SEQ ID NO. 10)-
5' CAATGAATTCATATGGGTTATGCACGTGCAGCAGCA 3';

and

SAKRP (SEQ ID NO. 11)-
5' CACGGATCCTTATTTCTTTTCTATAACAAC 3'.

The primer sets used for the generation of eGFP-PTD were as follows:

GFPRP (SEQ ID NO. 12)-
5' GTACGGATCCTTATCTAGATCCGGTGGATCCCGG 3';

GFPFP (SEQ ID NO. 13)-
5' GTACGAATTCATATGGTGAGCAAGGGCGAGGAG 3';

BTNTFP1GFP (SEQ ID NO. 14)-
5' GGTGGTGGTTCGGTGAGCAAGGGCGAG 3';

and

BTNTFP2GFP (SEQ ID NO. 15)-
5' CGTCAGGCGCGTGCGGGTGGTGGTTCGGTG 3'.

The primers BTNTFP3 and BTNTFP4 were common for amplification of both SAK-PTD and eGFP-PTD in the last two steps of the serial amplification.

Figure 2:
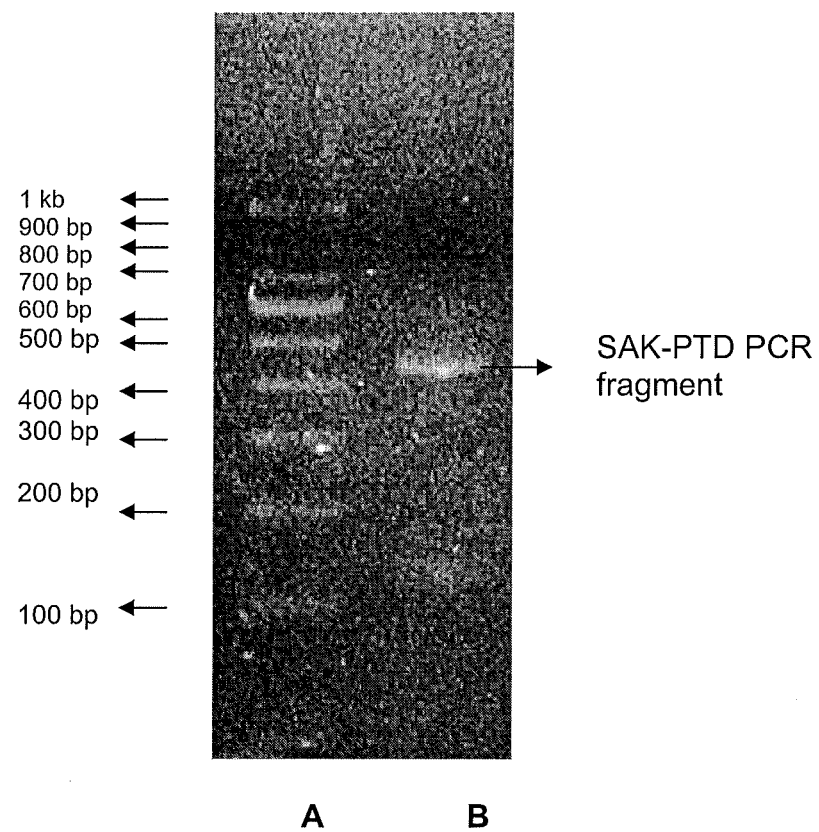
FIG. 2 shows in lane A 100 bp ladder, and in lane B the final PCR amplified product of SAK-PTD at about 429 bp.
Figure 3:
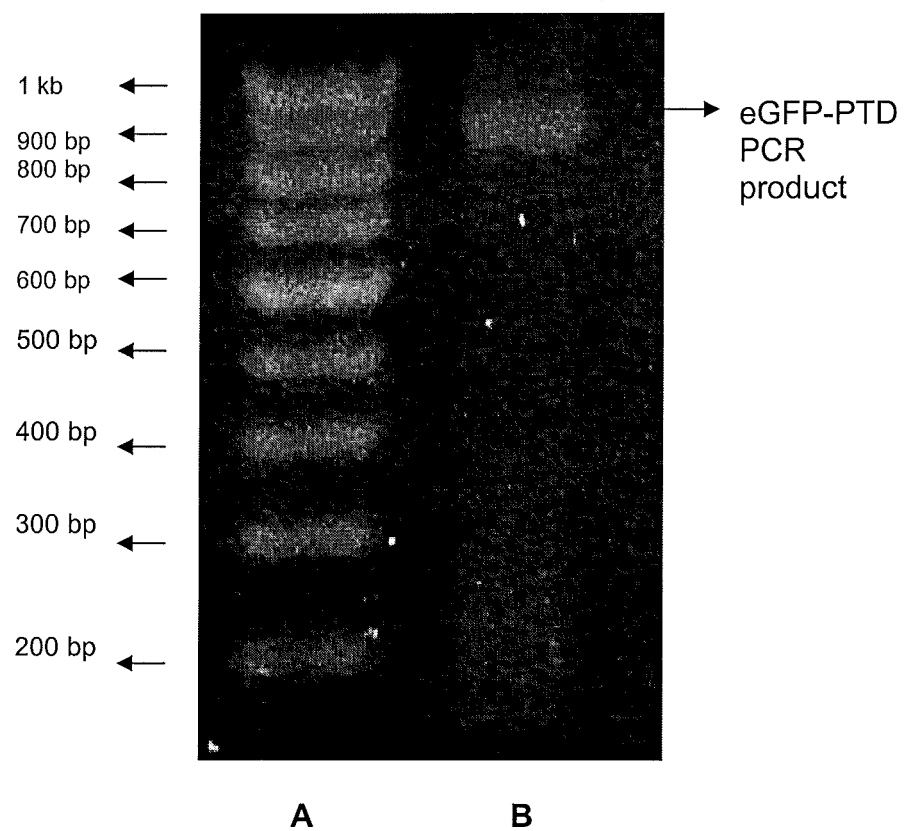
FIG. 3 shows in lane A 100 bp ladder, and in lane B the final PCR amplified product of eGFP-PTD.

SAK-PTD protein for further studies was purified from the soluble fraction. PCR amplification of the final SAK-PTD product is depicted in FIG. 2 and that of eGFP-PTD in FIG. 3. The final products of the amplification were gel purified from 1% agarose gel and were digested with EcoR1 and BamH1 and ligated by T4 DNA ligase into PGS100 vector under the control of a heat inducible promoter and cleaved with the same restriction enzymes. The ligated vector was transformed into E. coli DH5α strain by CaCl$_2$ method. Clone was confirmed by DNA sequencing by dideoxy chain termination method. E. coli strain DH5α for initial selection and amplification of the plasmids.

The recombinant plasmids containing SAK-PTD insert and eGFP-PTD inserts isolated from E. coli DH5α were transformed into E. coli host strain BL21 (λDE3) RIL strain for expression. Overnight cultures of E. coli BL21 DE3 RIL cells harboring the recombinant plasmid were diluted 1:50 in 1 liter of Luria Broth containing 50 μg/mL ampicillin. E. coli cells were grown at 30° C. with shaking to get an $A_{600}$ of 0.6, whereupon the expression of the target protein was induced by the raising the temperature of incubation to 42° C. Cells were harvested after 4 hr by centrifugation at 8,000 rpm for 10 min and the recombinant expression of SAK-PTD and eGFP-PTD were analyzed by 15% SDS-PAGE electrophoresis.

Figure 4:
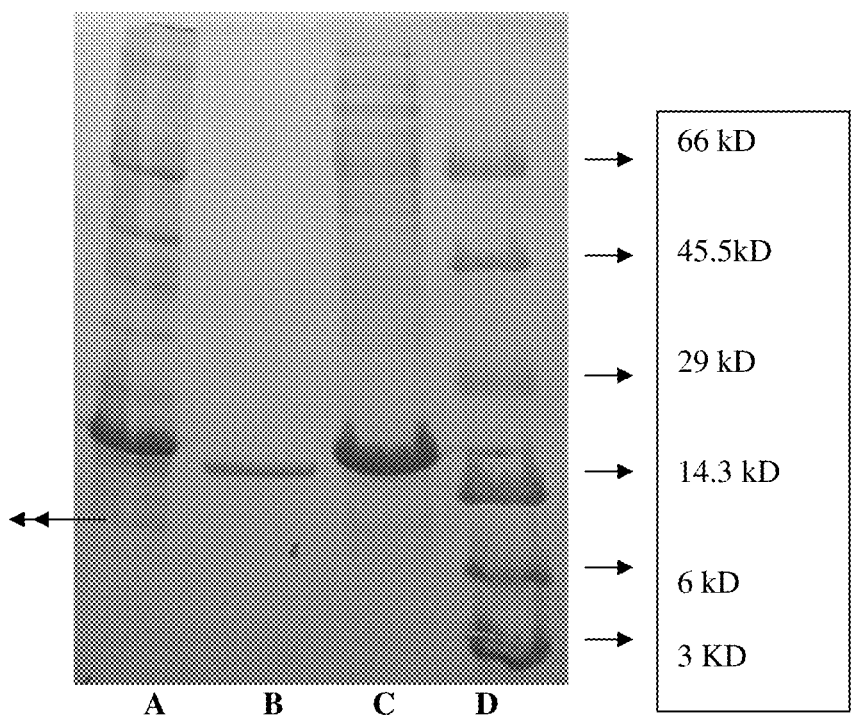
FIG. 4 shows expression of recombinant SAK-PTD in *E. coli* under a heat inducible promoter; in lane A, SAK-PTD protein expressed in inclusion bodies; in lane B, purified SAK protein; in lane C, SAK-PTD protein expressed as a soluble protein; and in lane D, molecular size marker.

The bacterial pellets were resuspended in buffer A (50 mM Tris-HC1 pH 7.4, 0.05 M NaC1, 0.5% TRITON-X-100™ (DECA(ETHYLENE GLUCOL)MONOOCTYLPHENYL ETHER), 10 mM EDTA and 5 mM PMSF). The cells were lysed by sonication at 15 microns amplitude for duration of 45 sec with an interval of 60 sec on ice for 35 cycles and the bacterial lysates were centrifuged at 8,000 g for 20 min to remove bacterial debris. The fraction present in the inclusion bodies were solubilized with 8M urea in the same buffer for 8 hours and dialysed in 10 mM Tris-HC1, pH 8.0 containing 1 mM EDTA. Major fraction of the SAK-PTD (see FIG. 4) and eGFP-PTD protein was expressed in the soluble fraction of the E. coli. Native eGFP cloned in PGS 100 was expressed and induced by heat induction at 42° C. for four hours. The protein expressed to a high level in the soluble fraction. Native staphylokinase gene cloned in pET23a vector was induced for four hours at 37° C. with 1 mM IPTG (isopropy1-1-thio-b-Dgalactopyranoside). Both native GFP and staphylokinase protein were used as the respective controls in the experiments involving in vitro cellular uptake of SAK-PTD and eGFP-PTD.

Example 3

Protein Purification: SAK-PTD and GFP-PTD

Figure 5:
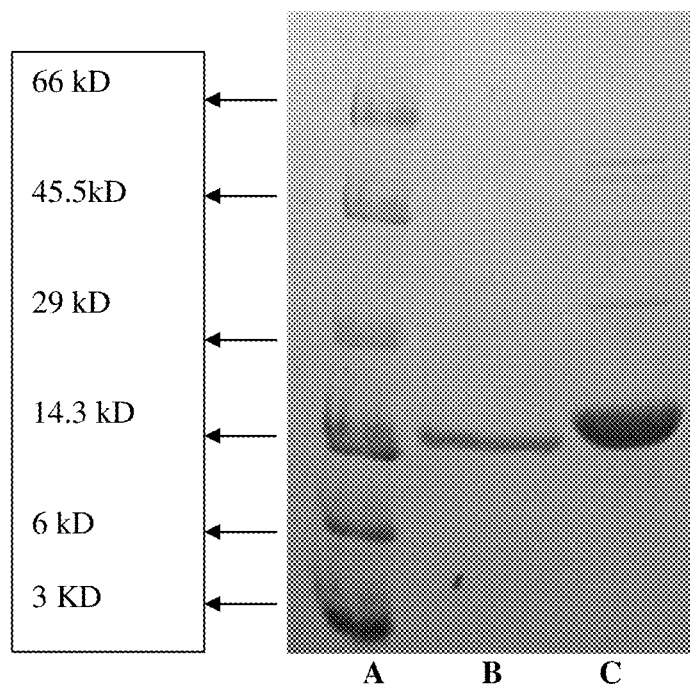
FIG. 5 shows the purified SAK and SAK-PTD proteins.
Figure 6:
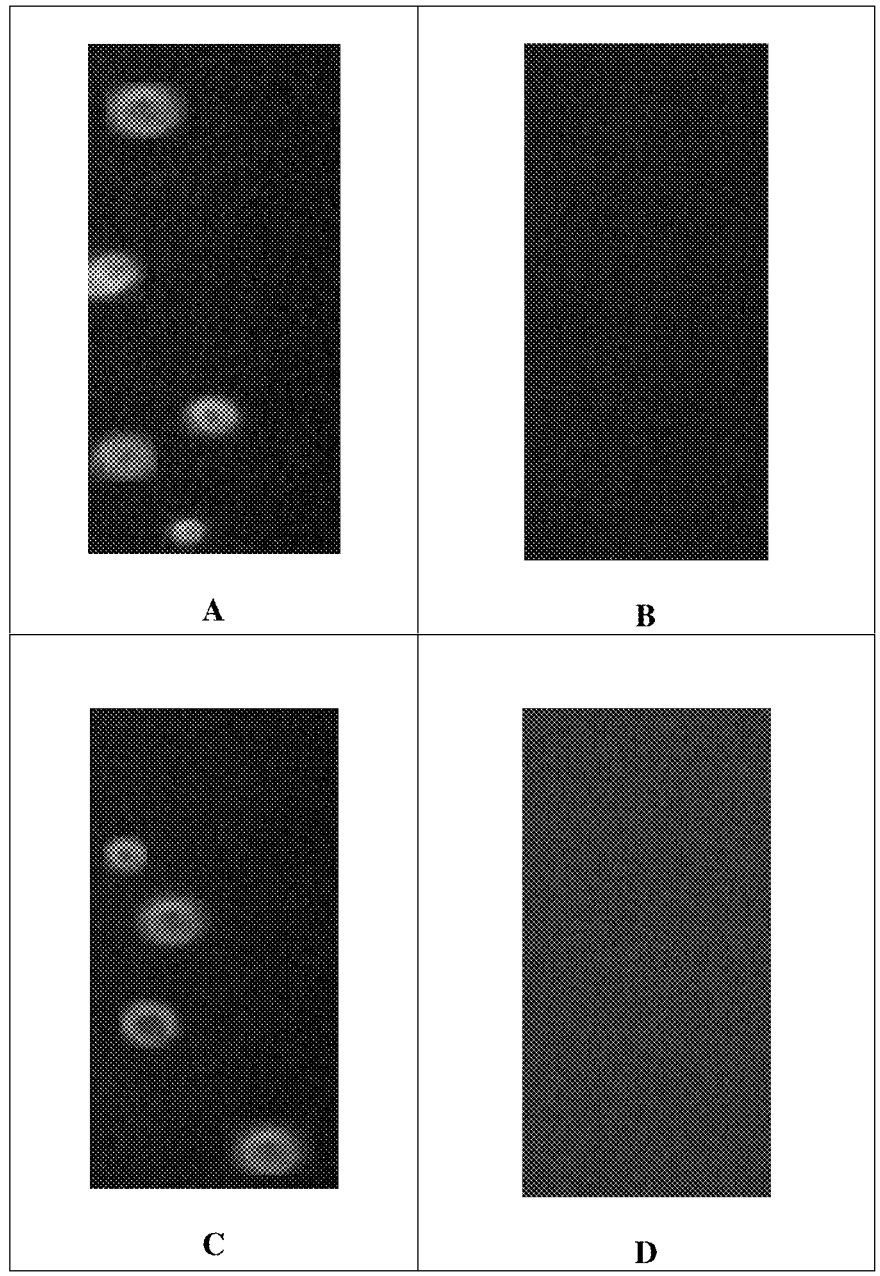
FIG. 6 shows in lane A, uptake of the purified eGFP-PTD into Vero cells after incubation at 37° C. for 30 min viewed under blue light in a fluorescent microscope; in lane B, eGFP control; in lane C, uptake of FITC-labeled SAK-PTD into Vero cells after incubation at 37° C. for 30 min; and in lane D, FITC-labeled SAK protein as control.

SAK-PTD protein expressed in the soluble fraction of the E. coli lysate was dialysed for 12 hours in 10 mM Tris-HCl buffer, pH 8.0 and loaded on a Q-sepharose column equilibrated with the same buffer. After washing the column with the buffer, elution was carried out with 50 mM-250 mM NaCl in the same buffer. SAK-PTD eluted with 70 mM NaCl. The fractions containing the protein were pooled and loaded on a phenyl sepharose column equilibrated with 10 mM Tris-HCl pH 8.0. After washing the column extensively with buffer containing 100 mM NaCl, the protein was eluted in water. eGFP that was expressed in the soluble fraction of the E. coli lysate was purified first on a Q-sepharose column equilibrated with 50 mM Tris-HCl buffer, pH 7.5 and eluted with NaCl in the same buffer at 150 mM. The fractions containing the protein were pooled and were loaded on a phenyl sepharose column equilibrated in 50 mM Tris-HCl buffer, pH 7.5. The column was extensively with 0.5M NaCl-20 mM NaCl in the same buffer and protein was eluted in buffer at low salt concentration. The protein was dialysed 10 mM phosphate buffer, pH 7.4 The purified protein fractions were pooled and analyzed on 12% SDS-PAGE. The purified SAK and SAK-PTD are depicted in FIG. 5. Staphylokinase and native eGFP protein were purified under similar conditions.

Example 4

FITC Conjugation of Staphylokinase and SAK-PTD Protein

To 1 mg/ml of the purified staphylokinase and SAK-PTD protein each, 1 M sodium carbonate-sodium bicarbonate buffer was added to a final concentration of 0.1 M. 5 µl of freshly prepared FITC solution was added with continuous and gentle mixing. The reactions vials were incubated for two hours at 37° C. and were protected from light. At the end of incubation, $\frac{1}{20}^{th}$ volume of 1 M ammonium chloride solution was added and incubated for 1 hour at room temperature. The FITC-conjugated proteins were eluted on a sephadex G-25 column equilibrated with 1×PBS (10 mM phosphate, pH 7.4 containing 154 mM NaCl). The absorbance of the fractions was monitored at $A_{280nm}$. The fractions containing FITC-conjugated SAK-PTD and native SAK were used for protein transduction studies in vitro.

Example 5

In order to study the effect of the addition of the PTD domain to staphylokinase and eGFP, in vitro cellular uptake studies of the native proteins and the PTD domain containing staphylokinase and eGFP were carried out in Vero cells and were visualized under a fluorescent microscope. Vero cells were seeded in 6 well tissue culture plates and cultured in DMEM (Dulbecco's Modified Eagle's Medium) containing 5% FBS (Fetal Bovine Serum) at 37° C. The cells when grown to about 70-80% confluence were washed twice with the same medium. In two separate experiments, the Vero cells were incubated with 50 µg of staphylokinase or SAK-PTD protein for 15 and 30 min at 37° C. in DMEM medium containing 1% FBS. At the end of incubation, the cells were washed at least three times in the same medium and visualized in a fluorescent microscope under blue light with or without fixing the cells with 4% formaldehyde for 30 min at room temperature. If the cells were fixed with formaldehyde, they were washed three times with PBS (10 mM phosphate, pH 7.4 containing 154 mM NaCl). The excitation wavelength was 450 nm to 490 nm and the emission was at 520 nm. In a parallel experiment similar study was conducted with eGFP and eGFP-PTD to study the effect of protein transduction domain on the cellular uptake of the proteins.

We claim:

1. A chimeric fusion protein comprising a thrombolytic protein and a protein transduction domain (PTD), wherein said protein transduction domain has the ability to transduce said thrombolytic protein across a cell membrane, wherein the thrombolytic protein is a mature staphylokinase having the amino acid sequence of SEQ ID NO: 1 and wherein the protein transduction domain is fused at any region of said thrombolytic protein, preferably at the N-terminus of the protein.

2. The chimeric fusion protein of claim 1, wherein the protein transduction domain consists of the amino acid sequence 5' YARAAARQARA 3' (SEQ ID NO: 4).

3. The chimeric fusion protein of claim 1, wherein the protein transduction domain consists of the amino acid sequence 5' YGRKKRRQRRR 3' (SEQ ID NO: 5).

4. A chimeric fusion protein comprising a thrombolytic protein and a protein transduction domain (PTD), wherein said protein transduction domain has the ability to transduce said thrombolytic protein across a cell membrane, wherein the thrombolytic protein is a mature staphylokinase having the amino acid sequence of SEQ ID NO: 2 and wherein the protein transduction domain is fused at any region of said thrombolytic protein, preferably at the N-terminus of the protein.

5. A chimeric fusion protein comprising a thrombolytic protein and a protein transduction domain (PTD), wherein said protein transduction domain has the ability to transduce said thrombolytic protein across a cell membrane, wherein the thrombolytic protein is a mature staphylokinase having the amino acid sequence of SEQ ID NO: 3 and wherein the protein transduction domain is fused at any region of said thrombolytic protein, preferably at the N-terminus of the protein.

6. The chimeric fusion protein of claim 1, further comprising a linker sequence of amino acids between the thrombolytic protein and the protein transduction domain allowing for proper folding of said thrombolytic protein and said protein transduction domain and wherein the linker consists of glycine and serine amino acid residues.

7. The chimeric fusion protein of claim 6, wherein said linker consisting of the sequence of SEQ ID NO: 6.

8. The chimeric fusion protein of claim 1, wherein the chimeric fusion protein is a recombinant protein expressed either in prokaryotic or eukaryotic expression system.

9. A pharmaceutical composition comprising the chimeric fusion protein of claim 1 and a buffer, wherein said buffer comprises any of the following: phosphate buffer, phosphate-citrate buffer, or any other pharmaceutically and physiologically acceptable buffer.

10. The chimeric fusion protein of claim 1, exhibiting transduction efficiency across cell membrane in vitro and therapeutic uptake into tissues when administered in vivo.

11. A method for dissolving blood clots in vasculature or tissues, comprising administering the chimeric fusion protein of claim 1 to a patient having blood clots.

12. A method of treating cerebral thrombosis, cerebral hemorrhage, or cerebral stroke, comprising administering the chimeric fusion protein of claim 1 to a patient having cerebral thrombosis, cerebral hemorrhage, or cerebral stroke.

13. A thrombolytic protein comprising a mature staphylokinase consisting of amino acid sequence SEQ ID NO:1.

14. A thrombolytic protein comprising a mature staphylokinase consisting of amino acid sequence SEQ ID NO:2.

15. A thrombolytic protein comprising a mature staphylokinase consisting of amino acid sequence SEQ ID NO:3.

16. A pharmaceutical composition comprising the chimeric fusion protein of claim 4 and a buffer, wherein said buffer comprises any of the following: phosphate buffer, phosphate-citrate buffer, or any other pharmaceutically and physiologically acceptable buffer.

17. A pharmaceutical composition comprising the chimeric fusion protein of claim 5 and a buffer, wherein said buffer comprises any of the following: phosphate buffer, phosphate-citrate buffer, or any other pharmaceutically and physiologically acceptable buffer.

18. A method for dissolving blood clots in vasculature or tissues, comprising administering the chimeric fusion protein of claim 4 to a patient having blood clots.

19. A method of treating cerebral thrombosis, cerebral hemorrhage, or cerebral stroke, comprising administering the chimeric fusion protein of claim 4 to a patient having cerebral thrombosis, cerebral hemorrhage, or cerebral stroke.

20. A method for dissolving blood clots in vasculature or tissues, comprising administering the chimeric fusion protein of claim 5 to a patient having blood clots.

21. A method of treating cerebral thrombosis, cerebral hemorrhage, or cerebral stroke, comprising administering the chimeric fusion protein of claim 5 to a patient having cerebral thrombosis, cerebral hemorrhage, or cerebral stroke.

* * * * *